(12) United States Patent
Appenzeller et al.

(10) Patent No.: US 9,072,559 B2
(45) Date of Patent: Jul. 7, 2015

(54) UNIVERSAL LENGTH SCREW DESIGN AND CUTTING INSTRUMENT

(71) Applicant: DePuy Synthes Products, Inc., Raynham, MA (US)

(72) Inventors: Andreas Appenzeller, Oberdorf (CH); Daniel Fluri, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 114 days.

(21) Appl. No.: 13/789,944

(22) Filed: Mar. 8, 2013

(65) Prior Publication Data

US 2014/0257413 A1 Sep. 11, 2014

(51) Int. Cl.
*A61B 17/86* (2006.01)
*A61B 17/88* (2006.01)

(52) U.S. Cl.
CPC ............ *A61B 17/863* (2013.01); *A61B 17/8863* (2013.01); *A61B 17/866* (2013.01)

(58) Field of Classification Search
CPC ...... A61B 17/86; A61B 17/88; A61B 17/863; A61B 17/8863
USPC ............................ 606/86 R, 300–331; 470/10
See application file for complete search history.

(56) References Cited

U.S. PATENT DOCUMENTS

| | | | |
|---|---|---|---|
| 4,016,874 A * | 4/1977 | Maffei et al. | 606/62 |
| 5,851,219 A * | 12/1998 | Goble et al. | 606/232 |
| 6,780,115 B2 * | 8/2004 | Schmieding et al. | 470/10 |
| 2003/0045881 A1 | 3/2003 | Barouk | |
| 2003/0229354 A1 | 12/2003 | Schmieding et al. | |
| 2004/0230195 A1 | 11/2004 | Kaikkonen | |
| 2010/0114315 A1 | 5/2010 | Manderson | |
| 2010/0211113 A1 * | 8/2010 | Olson et al. | 606/301 |

FOREIGN PATENT DOCUMENTS

DE 19943594 4/2001
WO WO 2005/079697 A1 9/2005

* cited by examiner

*Primary Examiner* — Christopher Beccia
(74) *Attorney, Agent, or Firm* — Baker & Hostetler LLP

(57) ABSTRACT

An adjustable length bone screw is provided that has a shaft that can be cut at any of several predetermined positions. The adjustable length bone screws can be provided in a kit containing many bone screws having the same or different initial lengths, and these screws can be cut to the desired length for use in the surgical procedure prior to, or during, the surgical procedure. The adjustable length bone screws have a plurality of threaded shaft sections that are separated by a plurality of unthreaded shaft sections along the length of the shaft. The threaded sections have preferably at least two cutting flutes extending longitudinally along the shaft. The invention provides the adjustable length bone screws, a tool for cutting the bone screws to a desired length, kits containing the bone screws and optionally the cutting tool, and methods for using the screws and/or the cutting tool in preparation for or during a surgical procedure.

10 Claims, 4 Drawing Sheets

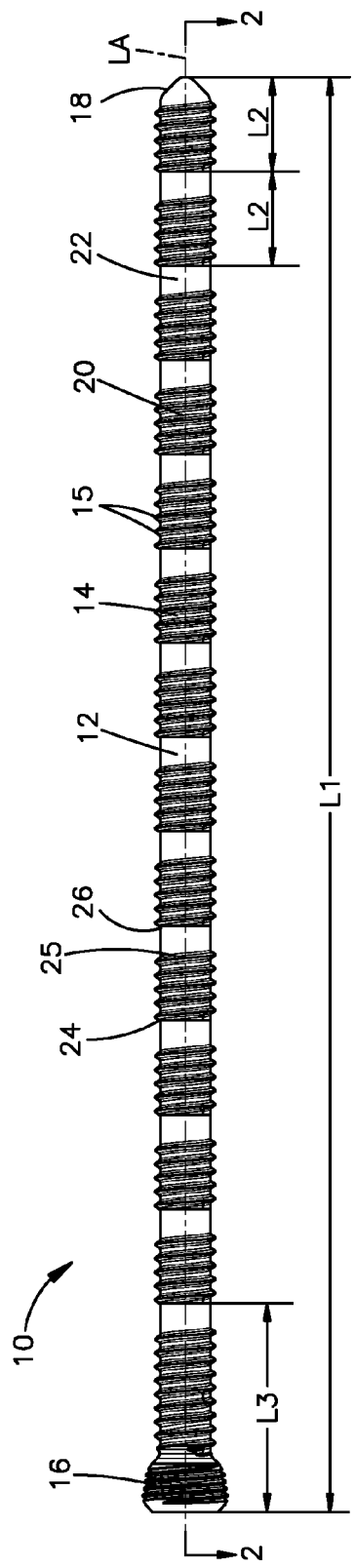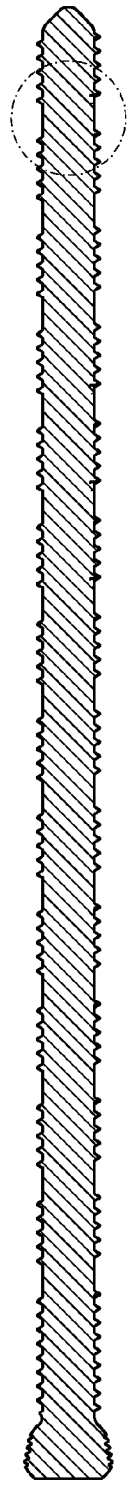

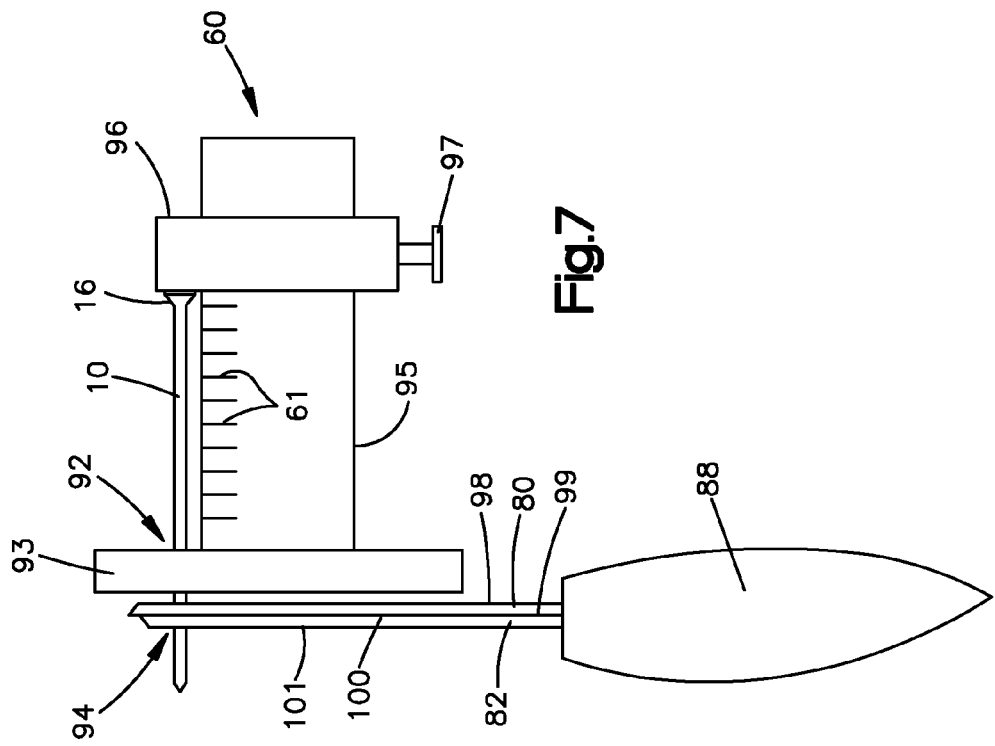
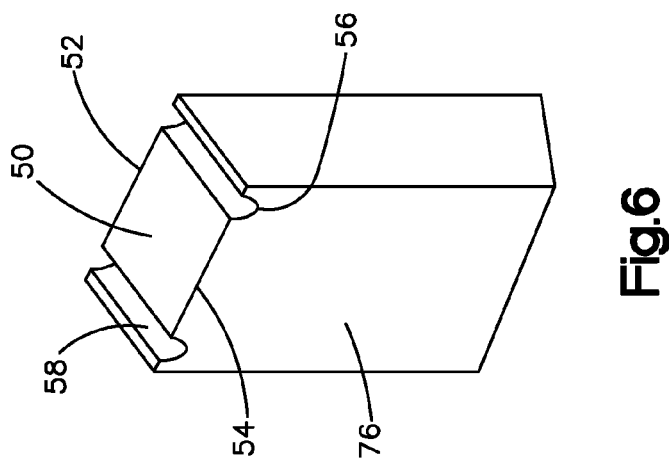

UNIVERSAL LENGTH SCREW DESIGN AND CUTTING INSTRUMENT

FIELD OF DISCLOSURE

The present invention generally relates to universal length bone screws and to instruments used to cut the screws to a proper length during or in preparation for a surgical procedure.

BACKGROUND

During many surgical procedures a surgeon is called upon to use a bone screw. A common example is when a bone plate is used to repair a bone fracture, and bone screws are used to secure the plate in place. The bone screws can be left in place with the bone plate until the bone has healed and then removed or left in place after that time.

The surgeon may be required to use various different lengths and sizes of bone screws for a particular surgical procedure. Thus, the surgical staff needs to carry a relatively large inventory of bone screws to have available for a procedure. Limiting these inventory needs would significantly reduce costs for a surgical outfit.

Bone screw designs and systems to address this problem have been proposed previously. For example, DE 19943594 A1 discloses one type of screw design having a plurality of separated thread segments where the screw can be separated between. Also, US 2003/0229354 A1 discloses a bone screw that can be cut with the aid of a cutting jig to adjust the length of the screw.

A need exists in the art to provide a bone screw design that can be readily cut before or during a surgical procedure to adjust the length of the screw to a desired length and where the screw is readily usable in the surgical procedure. A need also exists for a cutting instrument to be used to cut the screw to the desired length.

SUMMARY

The present invention relates to a universal length surgical bone screw design that can be adjusted to a desired length by the surgical staff either prior to, or during, the surgical procedure, an instrument or tool to cut the screw to its desired length, a kit containing a plurality of such screws and optionally the cutting tool, and a method for using the overall system during a surgical procedure.

The universal length bone screws can be adjusted for a desired length for use in a surgical operation where the screw is inserted into a bone. In one embodiment, the bone screw comprises a shaft section extending between a screw head and a shaft distal tip. The screw head has a length extending from a proximal end of the screw head to a distal end of the screw head where the screw shaft begins. The screw, and thus the screw shaft, has a longitudinal axis, preferably extending through the center of the screw, which preferably has a round outer periphery. The screw has a plurality of threaded portions located at discrete positions longitudinally along the shaft, and a plurality of unthreaded portions located at discrete positions longitudinally along the shaft, wherein the threaded portions are separated longitudinally by the unthreaded portions, and wherein the threaded portions contain a series of threads extending at least partially circumferentially around the shaft. The plurality of the threaded portions each can have at least one and preferably at least two cutting flutes each defined by a notch or recess formed radially into the screw shaft and extending longitudinally along the length of the threaded portions. The cutting flutes divide the threads of the threaded portions, preferably into at least two thread segments (corresponding to two flutes), extending circumferentially around the shaft such that the threading does not extend continuously circumferentially around the shaft.

The length of the bone screws can be adjusted by the surgical staff either during, or before, the surgical procedure. In one embodiment, the tool for cutting the adjustable length bone screw that is intended to be used with the cutting tool, the bone screw having an initial length, comprises a first arm and a second arm pivotally connected to the first arm. The tool can further comprise a first, elongated, open channel extending within the second arm in a lengthwise direction along the second arm and configured to accept the bone screw, the channel having a plurality of indicia to reflect a cut length of the bone screw that is less than the initial length of the screw. The tool can also contain a cutting blade coupled to either the first or second arm having an exposed cutting surface, wherein the cutting blade is positioned on the arm such that upon pivoting the first and second arms towards each other the cutting surface contacts the shaft of the bone screw to shear the bone screw shaft and to cut the bone screw to the cut length.

The invention also provides a kit containing a plurality of the adjustable length bone screws for use in a surgical operation or procedure where the screws are to be inserted into a bone. The kit can comprise a plurality of the adjustable length bone screws as described herein. The bone screws within the kit can each have the same initial length and desired segmented lengths for adjusting the length of the screw. The kit can also contain various initial length adjustable length bone screws as described herein and also various segment adjustment lengths for those various initial length screws.

Also, the invention provides various methods for conducting a surgical procedure. In an embodiment, there is a method for conducting a surgical procedure with a plurality of adjustable length bone screws where a surgical staff member cuts the length of at least one and preferably a plurality of adjustable length bone screws as described herein. The surgical staff then uses the cut length bone screw(s) in the surgical procedure by inserting the bone screw(s) into a bone. The screw(s) can be used to address a fracture with or without a fixation device such as a bone plate or an intramedullary rod or nail.

BRIEF DESCRIPTION OF THE DRAWINGS

The foregoing summary, as well as the following detailed description of certain preferred embodiments, are better understood when read in conjunction with the appended diagrammatic drawings. For the purpose of illustrating the invention, the drawings show those embodiments that are presently preferred. The invention is not limited, however, to the specific instrumentalities disclosed in the drawings. In the drawings:

FIG. 1 is a perspective view of a surgical bone screw according to an embodiment of the present disclosure;

FIG. 2 is a length-wise cross-sectional view of the bone screw shown in FIG. 1;

FIG. 6 is a perspective view of an embodiment of a cutting blade that can be used in the cutting tool of FIG. 6;

FIG. 7 is a perspective view of another embodiment of a cutting tool of the present invention;

DETAILED DESCRIPTION OF THE DRAWINGS

Figure 3:
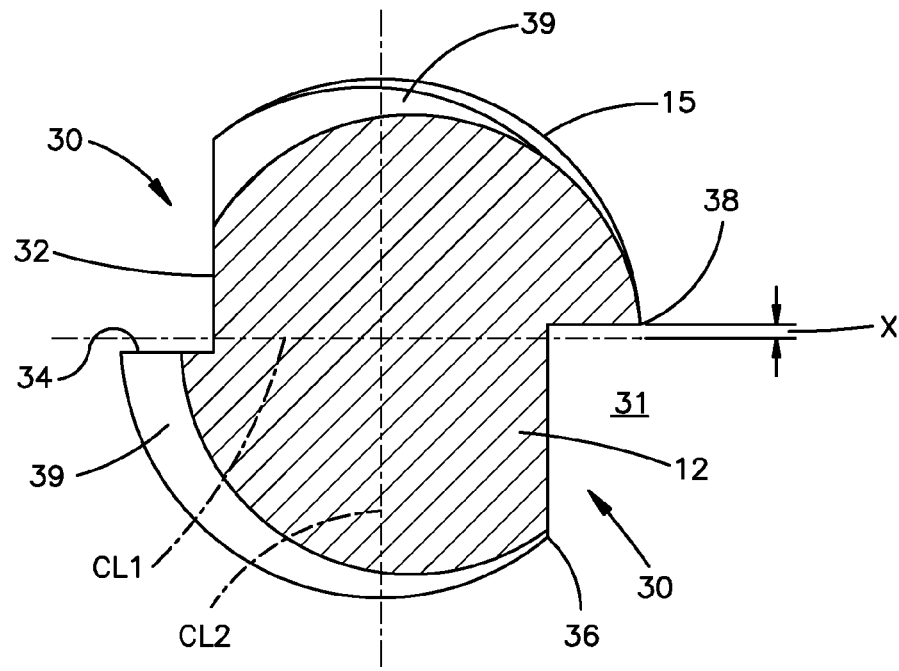
FIG. 3 is a cross-sectional view of the bone screw shown in FIG. 1.

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical equipment. The terminology includes the above-listed words, derivatives thereof and words of similar import.

With reference to FIG. 1 and longitudinal cross-section FIG. 2 from FIG. 1, there is shown a bone screw 10 in accordance with one embodiment of the present invention. Bone screw 10 has a shaft 12. The shaft 12 has a thread pattern 14. The bone screw 10 has a head 16 with at least one opening on its proximal face for engaging a driver, a distal tip 18, and a longitudinal axis LA. The screws can be provided in any thread diameter used in the industry, typical diameters are 1.0, 1.3, 1.5, 2.0, 2.4, 2.7, 3.5, 4.0, 4.5, and 6.5 mm. The screws are preferably constructed from metal, such as stainless steel or titanium. The screws can also be constructed from a bioabsorbable and biocompatible material, such as poly-L-Lactide acid (PLLA) or an equivalent material. The screw 10 can also be a lag screw that has no threading along a proximal section of the shaft 12 and the threading design described below along its distal section.

The shaft 12 of the bone screw 10 is designed to be cut into any of several lengths depending on the surgical need. As shown in FIG. 1, the bone screw 10 has a manufactured, initial, or first length L1 extending from the proximal end of the head 16 to the distal tip 18. The shaft 12 as depicted in FIG. 1 preferably has a discontinuous thread pattern 14. By discontinuous it is meant that the threads are present in discrete thread portions 20 along the length of the shaft 12 such that the shaft 12 also contains unthreaded portions 22. The thread portions 20 extend along the shaft 12 from a proximal start point 24 to a distal end point 25, and the unthreaded portions 22 terminate at distal point 26 and start at the point 25. In a preferred embodiment, the threaded 20 and unthreaded 22 portions are alternatively disposed beside each other.

As depicted in FIG. 1, the bone screw 10 can be cut or segmented into various lengths. The screw 10 has an initial length L1. The surgical staff can reduce the length of the screw 10 by cutting the screw 10 along its length at a point proximal to the tip 18. It is preferred that the surgical staff cut the screw 10 at a point along one of the unthreaded portions 22, and more preferably at the distal end point 26 of the unthreaded portion 22. As depicted in FIG. 1, the distance between the start 24 of a threaded portion 20 and the distal end of an adjacent unthreaded portion 26 can be a predetermined distance, L2. The distance L2 can be uniform along the length of the shaft 12, or it can be different for one or more sections L2. That is, as depicted, the distance L2 can be constant, or in other embodiments the shaft 12 can be constructed with various different lengths L2. In this manner, for example, the screw may have an original length of about 50 mm (L1) and have uniform L2 lengths of about 4 mm, such that the screw length can be shortened to lengths of 46, 42, 38, 34, 30 mm, etc.

The bone screws 10 of the present invention can have various initial L1 and incrementally shortened segment lengths depending on the designed and desired cut length L2. For example, the original length L1 can be anywhere from 10 to 150 mm, with segment increments L2 of anywhere between 2 and 10 mm, preferably either 2, 4 or 5 mm there between. For example, preferred initial lengths L1 for cortical bone screws are anywhere between 8 and 70 mm in intervals of 2 mm (e.g., 6, 8, 10, 12, etc. mm), and for these screws the segment increments L2 can be in either 2 mm or 4 mm increments. Particularly preferred cortical screws would have an initial length L1 of either 24, 40, 50, 60, or 70 mm and have segment increments L2 of either 2, 4, or 5 mm. And, for example, preferred initial lengths L1 for cancellous bone screws are anywhere between 8 and 150 mm in intervals of 2 mm (e.g., 6, 8, 10, 12, etc. mm), and for these screws the segment increments L2 can be in either 2 mm or 4 mm increments. Particularly preferred cancellous screws would have an initial length L1 of either 50 or 110 mm and have segment increments L2 of either 2, 4, or 5 mm. The bone screws can be conventional screws with integral shafts or screws with cannulated shafts.

The bone screw 10 can have any type of head design depending on the desired surgical application. For example, as shown in FIG. 1, the bone screw 10 is a locking screw having a threaded, conical head 16. Locking screw 10 can also have a rounded or spherical, threaded head 16. The screw 10 can also be a non-locking, conventional screw having an unthreaded head 16, preferably a rounded or spherical head 16 or a conical head 16. The screw 10 has an primary, shortest length L3 extending from the proximal end of the head 16 to the distal end of the first proximal unthreaded portion 22. In a preferred embodiment, the primary length L3 for the screw is about twice the length of the segment increment L2; thus, in one embodiment, the primary length L3 could be, for example, 8 mm and the segment increments L2 could be 4 mm such that the screw length could range from 8 mm to 12, 16, 20, etc. mm depending on the cut position distally from the proximal end of the head 16 (and this applies to all the lengths L1 and L2 described above).

As shown in FIG. 1 and better understood in FIG. 3, the threading present in the threaded portions 20 along the shaft 12 of the bone screw 10 is preferably a partial circumferential threading design. This partial circumferential threading means that the threads 15 that make up at least one, preferably a majority, and more preferably each of the threaded portions 20 along the shaft 12 contain at least one, and preferably a plurality of cutting flutes 30 that extend from the thread surface inwardly into the shaft 12 and also extend longitudinally along the shaft 12. The screw 10 preferably contains two oppositely opposed (180° separated) cutting flutes 30, however the number of cutting flutes can be one, two, three, four, five, or six or more and they can be equally spaced apart around the 360° shaft 12 surface or unequally spaced around the circumference of the shaft 12. The cutting flutes 30 thus divide the circumferential thread pattern 14 into discrete circumferential thread segments 39, the number of thread segments 39 generally being equal to the number of cutting flutes 30 or recesses 31. The cutting flutes 30 function to provide the screw 10 with a self-tapping capacity such that the screw 10 can be driven into a hole drilled into a bone more easily.

As shown in FIG. 3, in one embodiment, it is preferred that the shaft 12 contain two cutting flutes 30. The cutting flutes 30 can take any of a variety of geometrical shapes and are formed as notches or recesses 31 in the thread portions 20. The cutting flutes extend from a first edge 36 to a second edge 38. Preferably, the cutting flutes 30 are formed as 90° right-angle notch 31 between the first and second edges 36, 38 and have a first side wall 32 and a second side wall 34. However, the notches 31 forming the cutting flute 30 can have an obtuse or acute angle formed by side walls 32, 34, and the notch 31 forming the cutting flute 30 can have more than two side walls, such as three or four side walls. In another embodiment, the notch 31 forming the cutting flute extending from the first edge 36 to second edge 38 can be a curved surface, preferably a concave surface. The notches 31 forming the cutting flutes 30 for a single thread portion 20 are preferably the same geometrical shape, such as the right angle cut shown in FIG. 3; however they can be mixed between any of the shapes described herein. Furthermore, the notches 31 forming the cutting flutes 30 are preferably the same along the shaft 12 for each separate thread portion 20, however, as noted, each thread portion can have a mixed notch geometry and the recess geometry for the individual thread portions 20 can be different from one another and can be any combination of the above-described geometries. It is preferred that the notches 31, and thus the cutting flutes 30, extend parallel to the longitudinal axis LA of the screw shaft 12, however, the notches 31 can be formed into the shaft 12 in a substantially parallel manner to the longitudinal axis LA or the notches 31 can be formed at an angle of equal to or greater than 1°, 2°, 5°, 10°, 15°, 20°, 30°, or 45° from the longitudinal axis LA, with the angle preferably being less than 45° and more preferably less than 30°, and in some embodiments between 1° and 45°, preferably between 2° and 30°, and more preferably between 5° and 20°.

The depth of the notch or recess 31 forming the cutting flute 30, as shown in FIG. 3, is preferably such that in a first direction, such as for first side wall 32, the notch 31 extends beyond the center line CL1 of the shaft 12 diameter as shown by distance X. In a preferred embodiment, the distance X beyond the center line is about 0.05-0.25 mm, more preferably about 0.05-0.15, and even more preferably about 0.10 mm; the distance X can also be about 1 to about 10, preferably about 2 to about 6, and more preferably about 3 to about 5, percent of the diameter of the screw 10. For example, for a screw 10 having a 2.5 mm diameter, the distance X is about 0.1 mm. In another embodiment, the depth of a first side wall 32 of the recess 31 can be at least 10, preferably at least 15, and more preferably at least 20, percent of the screw shaft diameter, where the depth is measured in a direction from the shaft 12 surface parallel to a centerline for the screw (such as CL2) in the direction of the notch 31. The depth in a second, perpendicular direction along a second center line CL2 parallel to the first center line CL1 is preferably less than in the first direction; the depth of the notch 31 in this direction parallel to CL2 is preferably from about 5 to about 25, more preferably from about 10 to about 20, and more preferably about 12.5 to about 17.5, percent of the diameter of the shaft 12 of the screw 10. In this manner, the distance Y between the opposing first side walls 32 of two cutting flutes 30 as shown for the preferred embodiment in FIG. 3 is about 50 to about 90, preferably about 60 to about 80, and more preferably about 65 to about 75, percent of the shaft 12 diameter. In one embodiment, the cutting flutes extend the entire length of the threaded portion 20 in which the cutting flute is formed, however, the cutting flute can be formed only over a portion of the length of the threaded portion such as at least one, preferably at least two longitudinally aligned threads 15; that is, the cutting flute in one embodiment will extend along at least about 10%, 15%, 20%, 25%, 35%, 50% of the length of the individual threaded portion 20 in which it is present. In one embodiment, the cutting flute is formed along the entire length of the shaft 12 from the first distal-most threaded section 20 continuously through the adjacent threaded sections 20 and into the threaded section 20 adjacent the head 16 for at least one, two, or three consecutive longitudinally adjacent threads 15; that is, the notch 31 forming the cutting flute does not have to extend the entirety of each of the threaded sections 20.

Figure 4:
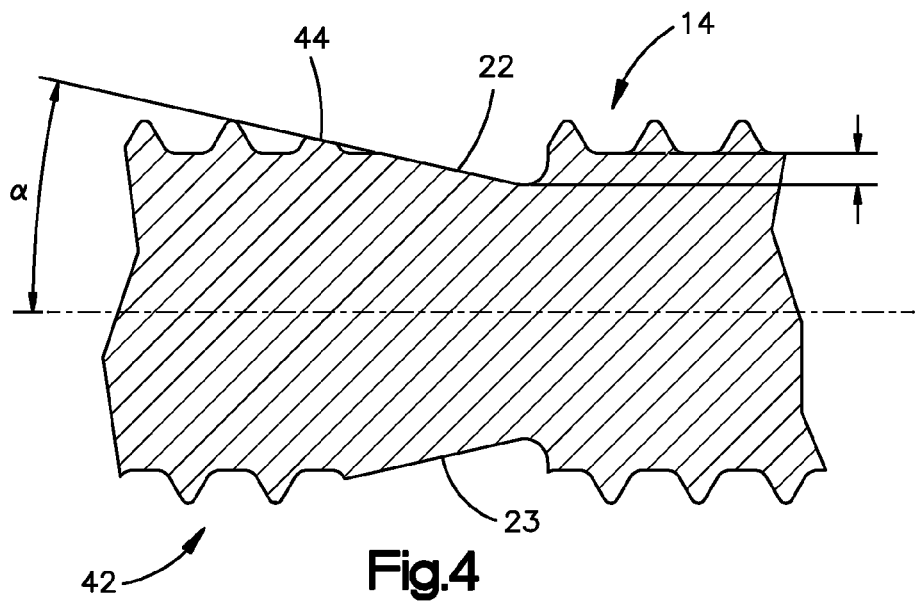
FIG. 4 is a detailed longitudinal cross-sectional view of the bone screw shown in FIG. 1.

In one embodiment of the invention, one or more of the threads 15 in the thread pattern 14 can be tapered along the distal portion 42 as shown in the enlarged portion W from FIG. 2 in FIG. 4. The tapered threads 44 are preferably those threads 15 that form the distal-most threads in a particular thread portion 20 for a particular thread segment 39. In practice, the tapered threads 44 will be at least one thread 15 in at least one thread segment 39. Preferably, however, the tapered threads 44 will be for at least one thread 15 for each thread segment 39 in a particular thread portion 20. It is also preferred that the tapered threads 44 be created for at least one thread 15 in each thread segment 39 for a plurality of the thread portions 20 along the shaft. In one embodiment, the tapered threads 44 will be for at least one thread 15 in at least one thread segment 39, or for each thread segment 39, for a majority of the thread portions 20 along the shaft. In another embodiment, the tapered threads 44 will be for at least one thread 15 in at least one thread segment 39, or for each thread segment 39, for each of the thread portions 20 along the shaft. For each of these previously described embodiments, the tapered threads 44 can extend over a plurality of threads 15 instead of at least one thread 15. The taper for the tapered threads 44 is preferably between an angle of 5° and 30°, more preferably between 10° and 30°, and most preferably between 15° and 25° from the longitudinal axis LA. as shown by angle α in FIG. 4. It is also preferred, as shown in FIG. 4, that the taper angle α extend along the unthreaded portion 22 such that the unthreaded portion 22 is tapered along its outer surface 23 from its proximal start to its distal end adjacent the next threaded section 20.

The screw 10 can be formed using various individual known manufacturing techniques in accordance with the novel procedural steps of the present invention. In one method, the screw 10 can be fully threaded along its shaft 12 with threads 15 in a conventional manner. Next, the shaft 12 can be milled to form the tapered threads 44, which process can also form the unthreaded portions 22. Next, the shaft 12 can be milled to make the notches or recesses 31 along the threaded portions 20 to form the cutting flutes 30. In an alternative method, the screw 10 can be fully threaded along its shaft 12 with threads 15 in a conventional manner, and next the shaft can be milled to make the notches or recesses 31 along the length of the shaft 12 to form the cutting flutes 30. Next, the shaft 12 can be milled to form the tapered threads 44, which process can also form the unthreaded portions 22.

Figure 5:
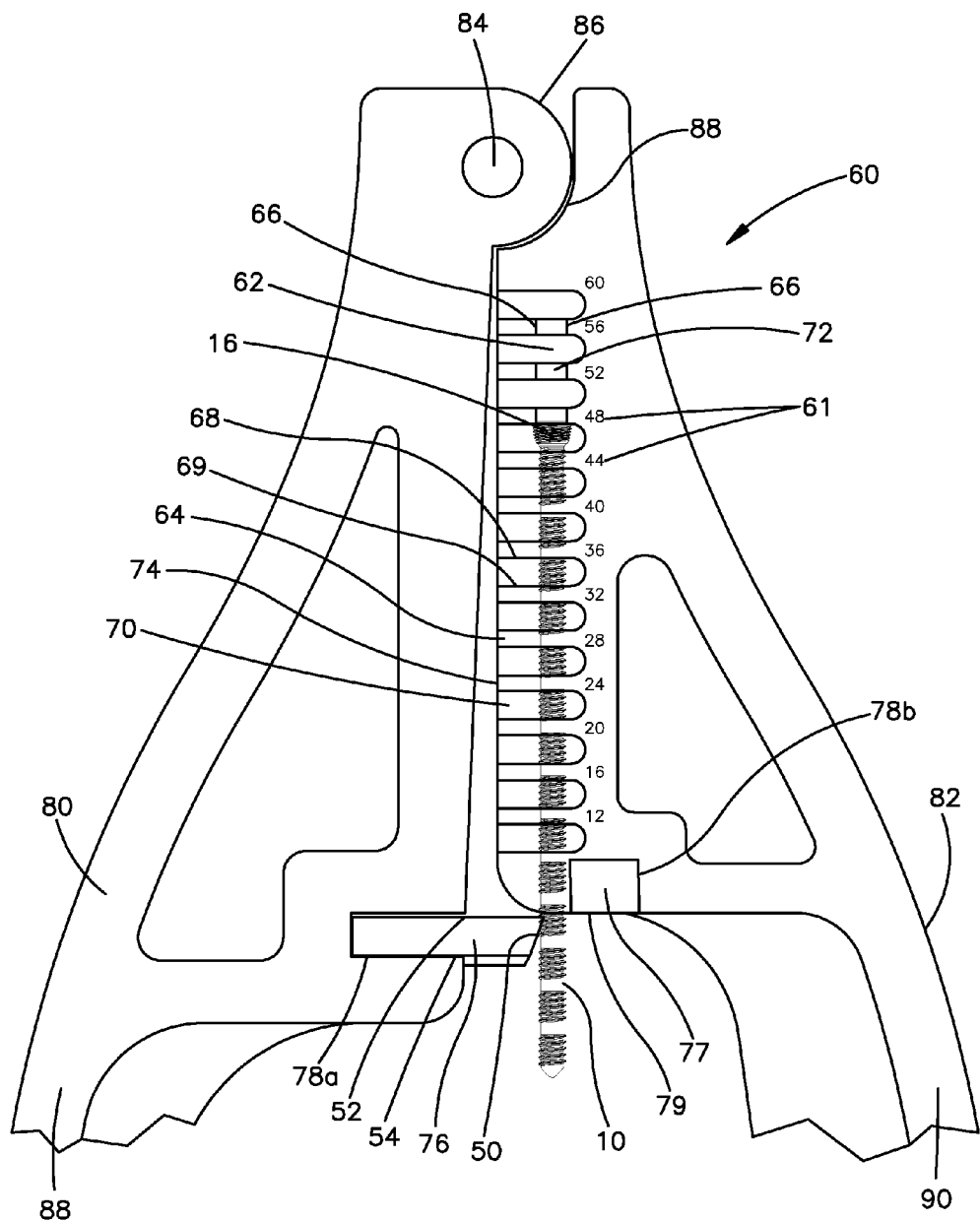
FIG. 5 is a perspective view of an embodiment of a cutting tool of the present invention.

The present invention also encompasses a cutting tool or instrument 60 used to cut the bone screw 10 to its proper length. As shown in FIG. 5, in one embodiment for the tool 60 the screw 10 is placed within a channel 62 extending along the length of one arm of the tool 60. The tool 60 preferably is constructed with a plurality of walls 64 having first side wall surfaces 68 and opposing second side wall surfaces 69—these side wall surfaces 68, 69 being formed substantially perpendicular to and preferably perpendicular to the longitudinal axis LA of the screw 10. The side wall surfaces 68, 69 have a height from a bottom surface 74 such that the opposing side wall surfaces 68, 69 form between them recesses 70 for receiving the threaded portions 20 of the screw shaft 12. The side wall surfaces 68, 69 can be straight or angled and can be curved either concave or convex. These recesses 70 have a depth that is preferably on the order of at least about 35%, more preferably at least about 50%, and even more preferably at least about 65% of the screw shaft 12 diameter to house the screw within the tool 60. Thus, for example, for screws having a 2.5 mm diameter, the recess 70 preferably has a depth of about 0.875, more preferably about 1.25, and even more preferably about 1.625 mm. The walls 64 have longitudinal recesses 72 to accept the unthreaded portions 22 of the screw shaft 12; these longitudinal recesses are formed by opposing longitudinal wall surfaces 66. These wall surfaces 66 can be in the form of straight or angled wall surfaces or the wall surfaces 66 can be a curved surface. The depth for the longitudinal recesses 72 is preferably the same as the depth for the recesses 70, but the depths for the two recesses can be different. The wall surfaces 66 are spaced oppose from one another to provide the recess with a width of about the diameter of the bone screw shaft 12. This width can be slightly less than the screw shaft diameter, particularly if the walls 64 are made of a resilient material that can expand to accept the screw in a snap-fit manner. The width of these walls 64 to define recess 72 can also be equal to or slightly greater than the screw shaft diameter to hold the screw.

The cutting tool 60 is designed to cut the bone screw 10 into various desired lengths. The tool 60 preferably contains a cutting blade 76. The blade 76 is housed within a chamber 78a defined within a first arm 80 of the tool 60. The tool 60 also preferably has a cutting block 77 against which the blade 76 can create a cutting force upon the screw 10. Preferably, the cutting blade 76 and block 77 are made of metal, and the other parts of the tool 60 can be made from such materials as metal, plastic, or other suitable materials. The cutting block 77 can be housed in chamber 78b in the second arm 82 of the tool 60. As shown, the cutting block 77 of the second arm is preferably located at the proximal portion of the channel 62, and the cutting blade 76 is preferably located such that its front surface 52 passes immediately adjacent the proximal portion of the channel 62 and in cutting fashion to the proximal face 79 of the cutting block 77. The tool has a second arm 82, which is pivotally coupled to the first arm 80 via pivot 84. The pivot 84 can be of any known construction such as a pivot pin that extends through the first and second arms 80, 82, where the first arm 80 has a first convex surface 86 and the second arm has a second concave surface 88 where these surfaces are designed to pivot about one another and where second arm 82 would have an extended distal portion (not shown) extending into a recess (not shown) in the first arm 80 at the pivot 84. The first 80 and second 82 arms have handles 88 and 90, respectively that can be grasped by a user to move the arms about the pivot 84. Although the tool 60 is depicted with the cutting blade 76 on the first arm 80 and the cutting block 77 on the second arm 82, these can be switched such that the cutting blade 76 is resized and configured to be housed within the chamber 78b on second arm 82 and the cutting block is resized and configured to be housed within the chamber 78a on first arm 80.

The cutting blade 76 preferably has a sharpened cutting edge 50 designed to cut the screw at a point near the distal end of an unthreaded portion 22. As shown in greater detail in FIG. 6, the cutting blade 76 has a cutting edge 50 that is preferably angled from a front 52 to a back 54 cutting blade surface. The angle for the cutting edge 50 can be at least about 10°, at least about 30°, or at least about 50°. In one embodiment, as seen in FIG. 6, the cutting blade 76 is designed with at least one cutting channel 56. The cutting channel 56 is formed as a recess into the cutting edge 50 defined by cutting blade walls 58. In this manner, the cutting blade 76 is designed such that the front surface 52 of the cutting edge 50 that contacts and cuts the screw shaft 12 is a curved or concave surface defined by the cutting walls forming the cutting channel 56. As the front, cutting surface 52 is forced against the screw shaft 12 by actuation of the handles 88, 90, the screw shaft 12 is cut and the distal, cut portion falls within the cutting channel 56.

As seen in FIG. 6, the cutting blade 76 can be constructed with two cutting channels 56. The channel 62 can be provided on both sides of the tool so that the indicia 61 can be different or the same. For example, on one side of the tool the indicia may be in an increment of 2, 4, or 6 mm and on the other side may be in an increment of 2, 4, or 6 mm, but the indicia may be different for the two opposite sides—for example one side may show 60 mm, 56 mm, 52 mm, 48 mm, etc. for a 4 mm increment and the other side may show 58 mm, 54 mm, 50 mm, etc. for a different level of the same 4 mm increment. The two grooves may be so that a screw can be cut into 2 mm increments according to an appropriate selection of the channel 62. In an alternative embodiment, the indicia 61 may be the same on each side. Thus, in one application, the tool 60 can be used to cut two screws 10 at once. That is, the tool 60 can be constructed such that it has the channel 62 associated to house a screw 10 on both sides of the tool. Thus, a surgical staff member can load the tool 60 with two screws at one time and actuate the handles 88, 90 to cut both screws 10 at once. The two screws so cut can have the same or a different length depending on the construction of the channel 62 and associated indicia 61.

Referring back to FIG. 5, to cut a screw a surgical staff member inserts the screw into the channel 62. The head 16 of the screw will be placed against the first side wall surface 68, which forms a shoulder against the top of the screw head 16; the tool 60 can include indicia 61 that indicate the final cut length for the screw 10. The tool 60 is preferably designed such that the wall surfaces 66 are made such that they are slightly resilient to form a snap-fit securement of the screw shaft 12. Next, the user can pivot the handles 88, 90 to bring the cutting blade 76 and its cutting edge 50 into contact with the screw shaft 12. Continued applied force with the handles will force the cutting blade 76 against the cutting block 77 and generate enough shear force to cut the screw shaft 12. The tool 60 is designed such that the cutting edge 50 of the cutting blade 76 passes proximally and adjacent to the proximal surface 79 of the cutting block 77.

FIG. 7 depicts another embodiment for the cutting tool 60. In this embodiment, the tool 60 has a first arm 80 connected to a first handle 88 and a second arm 82 connected to a second handle 90 (not shown, behind handle 88). The arms 80, 82 are pivotally attached such that actuation of the handles 88, 90 causes the arms 80, 82 to pivot relative to each other at their distal portions where the screw 10 is located. The screw 10 is positioned within an aperture 92 located within housing 93. The housing 93 is located adjacent to the first arm 80. First and second arms 80, 82 define an arm aperture 94 extending through the arms 80, 82 when the arms 80, 82 are in a first (non-cutting) position. Coupled to the housing 93 is a measuring block 95. The measuring block 95 carries indicia 61 for determining where to position the screw head 16. An adjustable slider 96 is adjustably positioned along the block 95 and secured into position with a set screw 97. In use, the surgical staff member places the screw 10 into the apertures 92, 94 and positions the head 16 at the desired indicia 61 location for the desired screw length. The slider 96 is then positioned against the screw head 16 and locked into position by the set screw 97. The handles 88, 90 are then actuated to cause the arms 80, 82 to pivot and snip the screw shaft 12 at the desired position. A cutting blade 76 (not shown) can be positioned either on the top surface 98 or bottom surface 99 of the first arm 80 or on the top surface 100 or bottom surface 101 of the second arm 82.

In performing a surgical procedure in accordance with the present invention, the surgeon would select an appropriate diameter screw 10 for the procedure. The surgeon would drill a hole in the bone where the screw is to be installed using an appropriately sized drill bit. The surgeon can countersink the bone hole to provide a surface for the head of the bone screw 10 if necessary (countersinking is not required if the screw 10 is being used, for example, to affix a bone plate to the bone surface). The surgeon can insert a depth gauge into the drilled hole to assist in determining the proper length for the bone screw 10. Optionally, the surgeon can pre-tap the hole. The surgeon would take a bone screw 10 having an initial length L1 greater than the desired length and using the cutting tool 60 cut the screw 10 to the desired length. The modified-length screw 10 is then used in the surgical procedure by advancing the screw 10 into the bone hole. The screws 10 can be used to repair bone fractures by inserting the screw 10 across a fracture site or by using the screw 10 to affix a bone plate to the bone surface approximate the bone fracture site as is well known in the art. This process can be repeated by the surgeon or the surgical staff for each bone screw 10 used in the procedure. The bone screw 10 can either be a standard, compression bone screw, a locking screw having a threaded head to lock with a bone plate, or a lag screw used to provide compression between two bone fragments.

The present invention also provides a surgical kit comprising a set of the bone screws 10 described herein. That is, the kit can contain a plurality of bone screws 10 each having the same initial length L1 or having a variety of initial lengths L1. In addition, the kit can also contain a plurality of screws 10 having different segment lengths L2. The kit can also contain various types of screws—standard, locking, lag, etc. The kit can contain any combination of these features—various initial lengths L1, various segment lengths L2, and various types of screws. Thus, the kit can have any variety of types of screws—standard, locking, lag, etc.—in various initial lengths L1 for each type of screw, and with various segment lengths L2 for each of the types and initial lengths L1 for the screws. Preferably, the kit will contain a single type of bone screw, such as a standard, locking, or lag screw, in a single initial length L1, and having a single segment length L2. In another embodiment, the kit will contain a single type of screw in a single initial length and having various segment lengths L2. In another embodiment, the kit will contain a single type of screw in more than one initial length L1 with either the same segment length L2 or different segment lengths L2.

It should be noted that the illustrations and discussions of the embodiments shown in the figures are for exemplary purposes only, and should not be construed limiting the disclosure. One skilled in the art will appreciate that the present disclosure contemplates various embodiments. It should be further appreciated that the features and structures described and illustrated in accordance one embodiment can apply to all embodiments as described herein, unless otherwise indicated. Additionally, it should be understood that the concepts described above with the above-described embodiments may be employed alone or in combination with any of the other embodiments described above.

What is claimed is:

1. An adjustable length bone screw for use in a surgical operation where the screw is inserted into a bone, the bone screw comprising:
   a screw head extending between a proximal end and a distal end and having an outer surface, and a shaft, the screw head and the shaft extending along a longitudinal axis, the shaft having a shaft outer surface and extending between the distal end of the screw head and a distal tip, wherein the outer surface of the screw head has a maximum diameter measured along a first direction that is perpendicular to the longitudinal axis that is greater than a maximum diameter of the shaft outer surface measured along the first direction;
   a plurality of threaded portions located at discrete positions longitudinally along the shaft, and a plurality of unthreaded portions located at discrete positions longitudinally along the shaft, wherein the threaded portions are separated longitudinally by the unthreaded portions, and wherein the threaded portions contain a series of threads extending at least partially circumferentially around the shaft;
   wherein the plurality of the threaded portions each have at least two cutting flutes each defined by a notch formed radially into the screw shaft and extending longitudinally along the length of the threaded portions such that the threads of the threaded portions are formed into at least two discontinuous thread segments extending circumferentially around the shaft, and
   wherein a plurality of the unthreaded portions are tapered along the shaft longitudinally in a proximal to distal direction and a plurality of the threaded portions proximally adjacent to the plurality of tapered unthreaded portions contain at least one thread that is tapered in the same angle as the taper for the adjacent unthreaded portion.

2. The adjustable length bone screw of claim 1, wherein for the tapered threaded portions each thread segment contains at least one tapered thread.

3. The adjustable length bone screw of claim 1 wherein the cutting flutes extend parallel to the longitudinal axis of the screw shaft.

4. The adjustable length bone screw of claim 1 wherein the notch for each of the cutting flutes for each of the plurality of threaded portions extends from the surface of the screw shaft to a point past a centerline for the screw shaft.

5. The adjustable length bone screw of claim 1 wherein the notch for each of the cutting flutes for each of the plurality of threaded portions extends from the surface of the screw shaft for a depth of at least 15% of the screw diameter measured in a direction parallel to a centerline for the screw shaft in the direction of the recess depth.

6. A kit of adjustable length bone screws for use in a surgical operation where the screws are inserted into a bone, the kit comprising:
   a plurality of adjustable length bone screws, each adjustable length bone screw comprising
      a screw head extending between a proximal end and a distal end and having an outer surface, and a shaft, the screw head and shaft extending along a longitudinal axis, the shaft having a shaft outer surface and extending between the distal end of the screw head and a distal tip, wherein the outer surface of the screw head has a maximum diameter measured along a first direction that is perpendicular to the longitudinal axis that is greater than a maximum diameter of the shaft outer surface measured along the first direction;
      a plurality of threaded portions located at discrete positions longitudinally along the shaft, and a plurality of unthreaded portions located at discrete positions longitudinally along the shaft, wherein the threaded portions are separated longitudinally by the unthreaded portions, and wherein the threaded portions contain a series of threads extending at least partially circumferentially around the shaft;

wherein the plurality of the threaded portions each have at least two cutting flutes each defined by a recess formed radially into the screw shaft and extending longitudinally along the length of the threaded portions, and wherein the cutting flutes divide the threads of the threaded portions into at least two thread segments extending circumferentially around the shaft such that the threading does not extend continuously circumferentially around the shaft wherein a plurality of the unthreaded portions are tapered along the shaft longitudinally in a proximal to distal direction and a plurality of the threaded portions proximally adjacent to the plurality of tapered unthreaded portions contain at least one thread that is tapered in the same angle as the taper for the adjacent unthreaded portion wherein the adjustable length bone screws each have an initial length defined by the distance between the proximal end of the head and the distal tip.

7. The kit of claim 6 wherein the kit contains only adjustable length bone screws having the same initial length.

8. The kit of claim 6 wherein the kit contains a plurality of adjustable length bone screws having a first initial length and a plurality of adjustable length bone screws having a second initial length that is longer than the first initial length.

9. A method for conducting a surgical procedure with a plurality of adjustable length bone screws each having an initial length, the method comprising the steps of:
(a) cutting the initial length of an adjustable length bone screw to form a cut length bone screw having a length less than the initial length, where the adjustable length bone screw comprises
a shaft extending between a screw head having a proximal end and a distal tip, where the shaft section has a longitudinal axis;
a plurality of threaded portions located at discrete positions longitudinally along the shaft, and a plurality of unthreaded portions located at discrete positions longitudinally along the shaft, wherein the threaded portions are separated longitudinally by the unthreaded portions, and wherein the threaded portions contain a series of threads extending at least partially circumferentially around the shaft;
wherein the plurality of the threaded portions each have at least two cutting flutes each defined by a recess formed radially into the screw shaft and extending longitudinally along the length of the threaded portions, and
wherein the cutting flutes divide the threads of the threaded portions into at least two thread segments extending circumferentially around the shaft such that the threading does not extend continuously circumferentially around the shaft;
(b) using the cut length bone screw in the surgical procedure by inserting the cut length bone screw into a bone.

10. A method for manufacturing a plurality of adjustable length bone screws, the method comprising the steps of:
(a) making a bone screw having a proximal head having a maximum head diameter, a shaft having a maximum shaft diameter, and a distal tip, wherein the maximum head diameter is greater than the maximum shaft diameter;
(b) forming a plurality of threaded portions having a proximal and a distal end along the shaft;
(c) forming a first and a second notch cut into the shaft along the length of each one of the plurality of threaded portions at the respective distal end to form two cutting flutes therein, such that each one of the plurality of threaded portions has two discontinuous circumferential thread segments along its respective length;
(d) forming a plurality of unthreaded portions extending longitudinally along the shaft where a plurality of the threaded portions are bounded on both the proximal and distal end by an unthreaded portion; and
(e) forming a tapered region at a first angle along the shaft longitudinally in a proximal to distal direction in a plurality of the plurality of unthreaded portions and forming a taper at a second angle in a plurality of the plurality of threaded portions where the first angle is the same as the second angle.

* * * * *